(12) United States Patent
Sukkau et al.

(10) Patent No.: US 12,127,855 B2
(45) Date of Patent: Oct. 29, 2024

(54) DC MOTOR WITH ANGLE SENSOR, ROTOR WITH WINDINGS AND ROTARY TRANSMITTER FOR DC MOTOR, COUCH FOR MAGNETIC RESONANCE SYSTEM, AND METHOD FOR OPERATING A DC MOTOR WITH ANGLE SENSOR

(71) Applicant: Siemens Healthcare GmbH, Erlangen (DE)

(72) Inventors: Johann Sukkau, Herzogenaurach (DE); Christopher Horn, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 534 days.

(21) Appl. No.: 17/470,011

(22) Filed: Sep. 9, 2021

(65) Prior Publication Data
US 2022/0071564 A1   Mar. 10, 2022

(30) Foreign Application Priority Data
Sep. 9, 2020   (DE) .......................... 102020211327.0

(51) Int. Cl.
*H02K 11/33*    (2016.01)
*A61B 5/00*     (2006.01)
(Continued)

(52) U.S. Cl.
CPC .............. *A61B 5/704* (2013.01); *A61B 5/055* (2013.01); *H02K 11/215* (2016.01); *H02K 11/33* (2016.01); *H02K 29/08* (2013.01)

(58) Field of Classification Search
CPC ........ A61B 5/704; A61B 5/055; H02K 11/21; H02K 11/22; H02K 11/215; H02K 11/33;
(Continued)

(56) References Cited

U.S. PATENT DOCUMENTS 2,118,313 A * 5/1938 Kongsted ............... H02K 19/24
                                                  310/155
4,030,005 A    6/1977 Doemen
(Continued)

FOREIGN PATENT DOCUMENTS

CN   107112875 A    8/2017
DE   102004036316 A1  2/2005
(Continued)

OTHER PUBLICATIONS

WO-2005062432-A1 English Translation (Year: 2005).*
(Continued)

*Primary Examiner* — Maged M Almawri
(74) *Attorney, Agent, or Firm* — Banner & Witcoff Ltd.

(57) ABSTRACT

A direct current (DC) motor for operation in an external magnetic field may include a rotor which is rotatable about a rotation axis and has at least two windings, at least four continuous rotary transmitters, wherein two rotary transmitters are associated with each of the windings and are configured to supply the associated winding with direct current, an angle sensor which is configured to determine the angular position of the rotor, and a controller configured to control the current feed to at least one of the windings dependent upon the angular position of the rotor. The motor is oriented relative to an external magnetic field during operation so that the rotation axis extends transversely to the external magnetic field.

18 Claims, 5 Drawing Sheets

Figure 1:
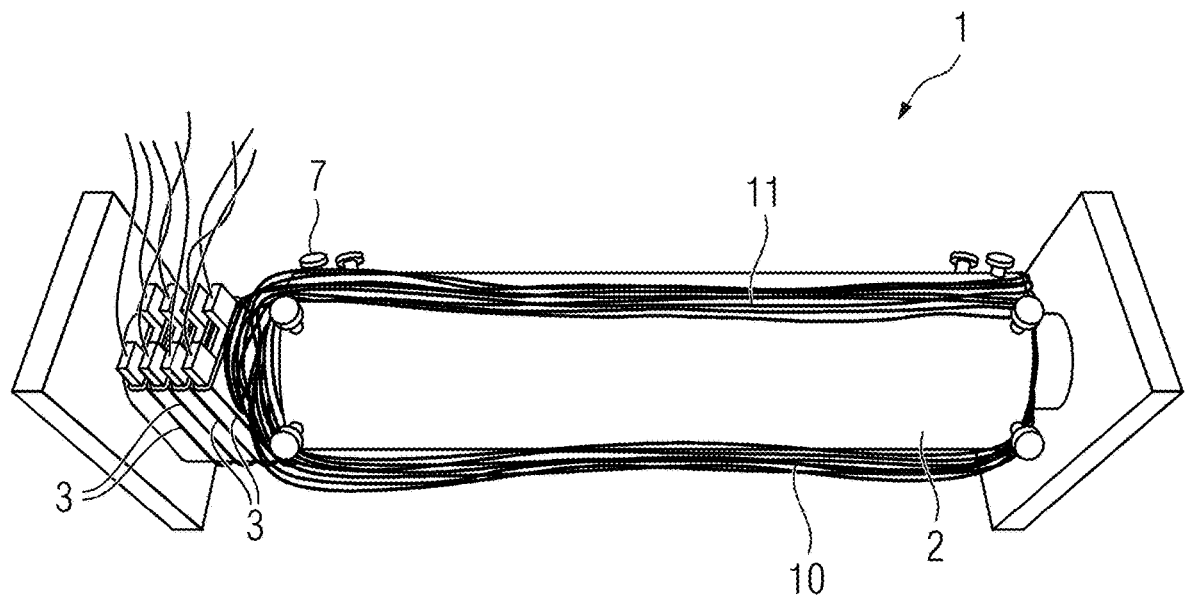

(51) Int. Cl.
*A61B 5/055* (2006.01)
*H02K 11/215* (2016.01)
*H02K 29/08* (2006.01)

(58) Field of Classification Search
CPC .... H02K 29/08; H02K 29/10; H02K 2213/03; H02P 21/22; H02P 6/16; H02P 6/24
USPC .............. 310/261.1–269, 128, 127, 130, 143
See application file for complete search history.

(56) References Cited

U.S. PATENT DOCUMENTS

| | | | | |
|---|---|---|---|---|
| 4,902,975 | A | | 2/1990 | Kess |
| 5,066,915 | A | * | 11/1991 | Omori .................... A61B 5/704 |
| | | | | 324/318 |
| 6,708,503 | B1 | * | 3/2004 | Wang ...................... H02K 55/04 |
| | | | | 62/51.1 |
| 6,711,421 | B2 | * | 3/2004 | Wang ........................ H02K 3/04 |
| | | | | 505/166 |
| 7,352,096 | B2 | * | 4/2008 | Dunn ...................... H02K 53/00 |
| | | | | 310/156.43 |
| 7,476,999 | B2 | * | 1/2009 | Friedland ............... H02K 33/18 |
| | | | | 310/264 |
| 8,162,037 | B2 | * | 4/2012 | Kruip ................. G01R 33/3804 |
| | | | | 62/51.1 |
| 10,330,754 | B2 | | 6/2019 | Garcia et al. |
| 11,650,275 | B2 | * | 5/2023 | Horn ...................... H02K 37/00 |
| | | | | 324/318 |
| 11,821,970 | B2 | * | 11/2023 | Bindseil ............. G01R 33/3856 |
| 2004/0005027 | A1 | | 1/2004 | Nafstadius |
| 2004/0080229 | A1 | | 4/2004 | Haner |
| 2005/0023475 | A1 | | 2/2005 | Li et al. |
| 2006/0125345 | A1 | * | 6/2006 | Lee ........................ H02K 23/40 |
| | | | | 310/264 |
| 2007/0043288 | A1 | * | 2/2007 | Mueller ............... G01R 33/287 |
| | | | | 600/411 |
| 2008/0024034 | A1 | * | 1/2008 | Koizumi ................ H02K 16/02 |
| | | | | 310/90 |
| 2009/0093369 | A1 | * | 4/2009 | Kwon .................... H02K 55/06 |
| | | | | 310/46 |
| 2010/0317201 | A1 | * | 12/2010 | Denk ................... H01R 39/646 |
| | | | | 439/5 |
| 2011/0025239 | A1 | * | 2/2011 | Epstein .................. H02K 53/00 |
| | | | | 310/156.43 |
| 2013/0147310 | A1 | | 6/2013 | Safari Zadeh |
| 2013/0225415 | A1 | * | 8/2013 | Kim ........................ H02K 3/24 |
| | | | | 156/60 |
| 2015/0015262 | A1 | * | 1/2015 | Greim .................. G01R 33/385 |
| | | | | 324/322 |
| 2016/0116562 | A1 | * | 4/2016 | Utsumi .............. G01R 33/3858 |
| | | | | 324/309 |
| 2017/0244345 | A1 | | 8/2017 | Huwiler et al. |
| 2018/0120394 | A1 | * | 5/2018 | Seeber ............... G01R 33/3858 |
| 2018/0188340 | A1 | * | 7/2018 | Garcia ................. H02K 13/006 |

FOREIGN PATENT DOCUMENTS

| | | | | |
|---|---|---|---|---|
| DE | 60309207 | T2 | 8/2007 | |
| DE | 102009018655 | A1 | 10/2010 | |
| DE | 102009038685 | A1 | 3/2011 | |
| DE | 102009060544 | A1 | 6/2011 | |
| DE | 102017131317 | A1 | 7/2018 | |
| DE | 202020104661 | U1 | 9/2020 | |
| EP | 2498347 | A1 | 9/2012 | |
| KR | 20100028250 | A | 3/2010 | |
| WO | WO-2005062432 | A1 * | 7/2005 | ............ H01R 39/30 |
| WO | 2007147657 | A1 | 12/2007 | |

OTHER PUBLICATIONS

English Translation (Year: 2005).*
German Action dated May 19, 2021, Application No. 10 2020 211 327.0.
1 European Search Report for Application No. 10 2020 211 327.0 dated Sep. 21, 2020.
Cheng Zhou, "Electric Machines and Electric Control (For the Specialism of Electronic Technology Applications)"; Higher Education Press; Jul. 31, 2003; pp. 35-40.

* cited by examiner

DC MOTOR WITH ANGLE SENSOR, ROTOR WITH WINDINGS AND ROTARY TRANSMITTER FOR DC MOTOR, COUCH FOR MAGNETIC RESONANCE SYSTEM, AND METHOD FOR OPERATING A DC MOTOR WITH ANGLE SENSOR

CROSS REFERENCE TO RELATED APPLICATIONS

This patent application claims priority to German Patent Application No. 10 2020 211 327.0, filed Sep. 9, 2020, which is incorporated herein by reference in its entirety.

BACKGROUND

In a couch of a magnetic resonance (MR) tomography unit (scanner), a motor is used to move the couch in the vertical and horizontal direction. It is known in the prior art to use an electric servomotor for this purpose. This motor is implemented as a brushless motor in which the stator consists of a plurality of windings and the rotor is equipped with permanent magnets. Due to the permanent magnets, when such motors are used in spatial proximity to external magnetic fields (such as, for example, a magnetic field of an MR tomography unit), care must be taken that they do not come too close to the origin generating the external magnetic field.

Currently, for example, couches of MR systems are provided with a spacing frame which mechanically prevents the couch from approaching the magnet of the MR tomography unit too closely. The motors themselves are accommodated in the rear part of the couch and a strong anchoring is provided in order to fix the motor in place in a couch chassis. The torque of such motors is proportional to the magnetic flux density of the permanent magnets in the rotor. Due to the aforementioned problem of spacing from the MR magnets, such motors are therefore limited in their size and torque to a particular value.

The conventional alternatives, such as pneumatic or piezo motors, are either too slow, too weak or too expensive for use in a couch of an MR system. Purely electric motors therefore appear more advantageous.

From U.S. Pat. No. 4,902,975 A, there is known a direct current (DC) motor which has a plurality of windings on a rotor, which windings can be supplied with current via sliding contacts. The sliding contacts are interrupted at a plurality of sites so that the commutation—as is usual in DC motors—takes place mechanically. In addition, the motor uses an external magnetic field as the stator field.

From U.S. Ser. No. 10/330,754 B2 also, there is known a motor for use in an external magnetic field. The motor has sliding contacts and an inverter which rotates with a rotor, by means of which windings on the rotor are supplied with current.

For a high-precision drive, also of power-intensive apparatuses (for example, couches of an MR system), however, powerful and exactly controllable motors, the rotary angle of which can be exactly predetermined, are required.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 2:
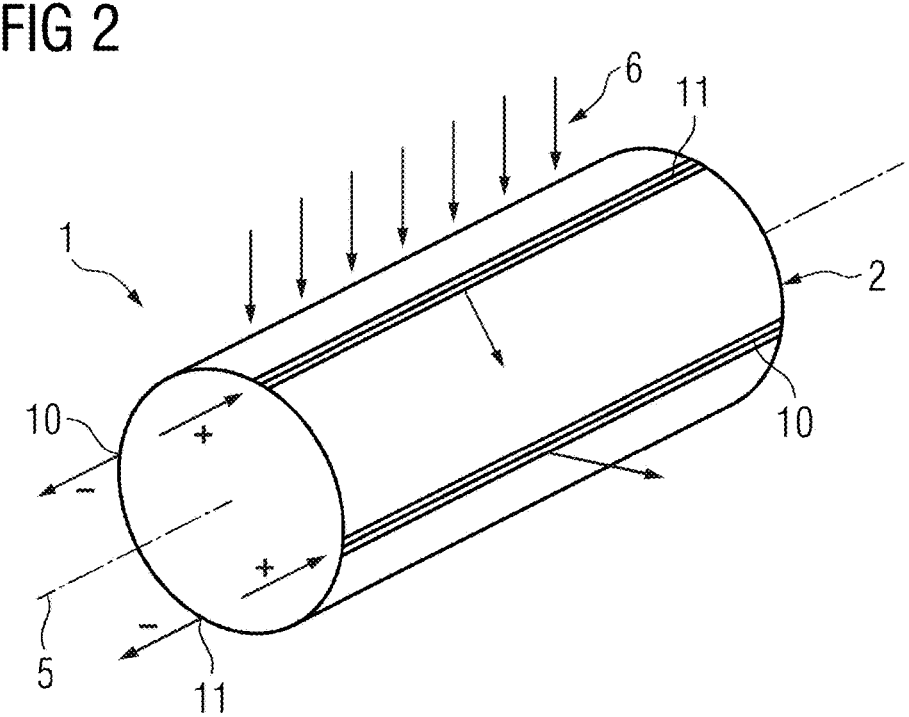
Figure 3:
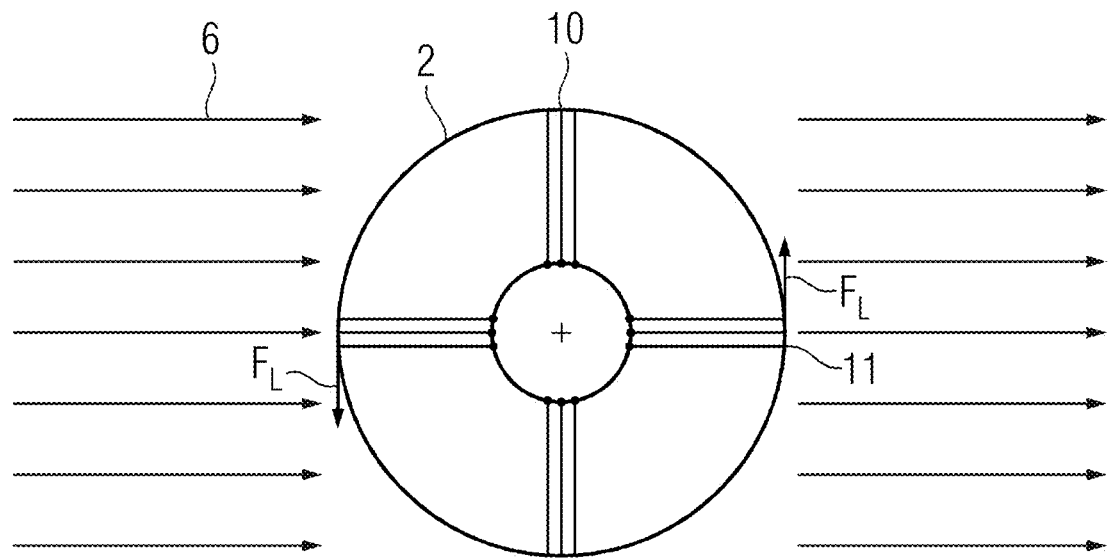
Figure 4:
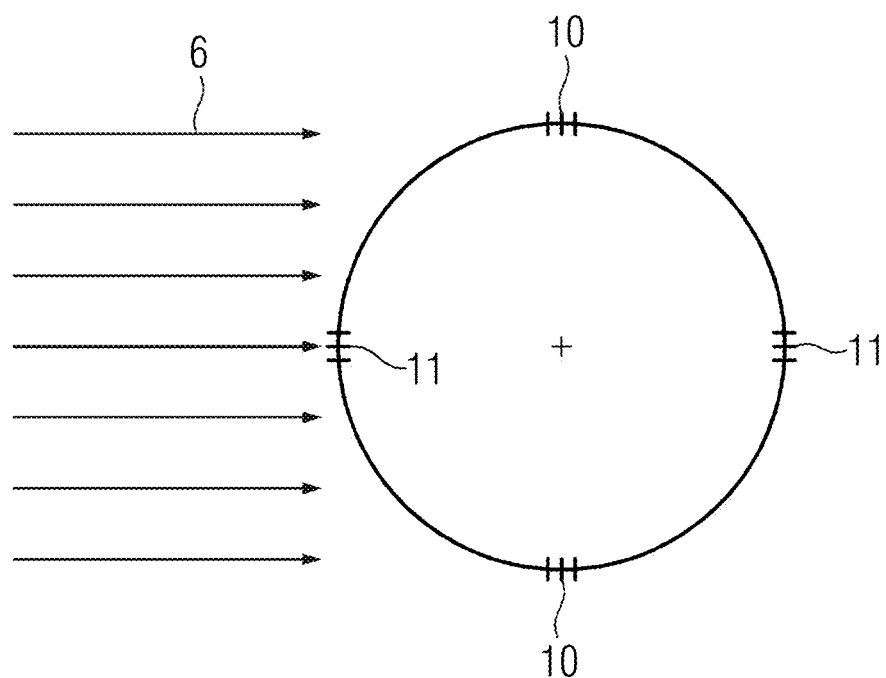
Figure 5:
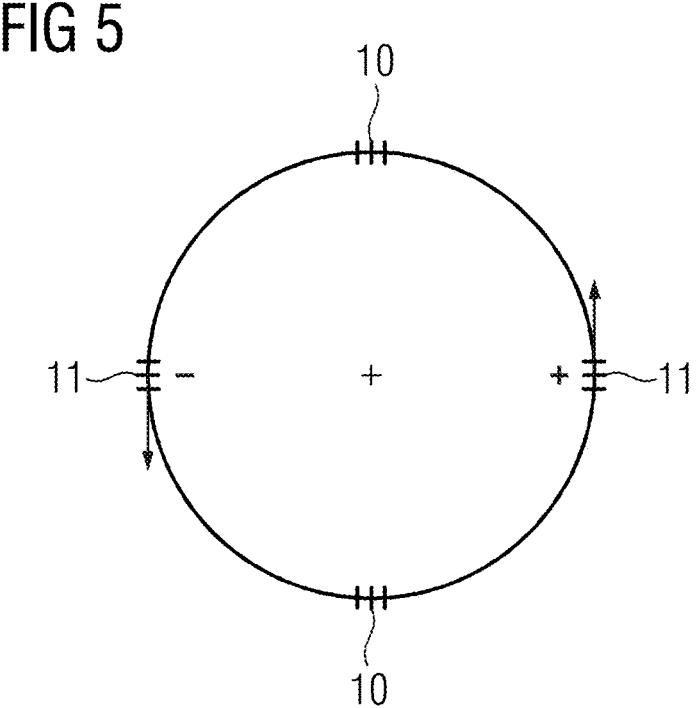
Figure 6:
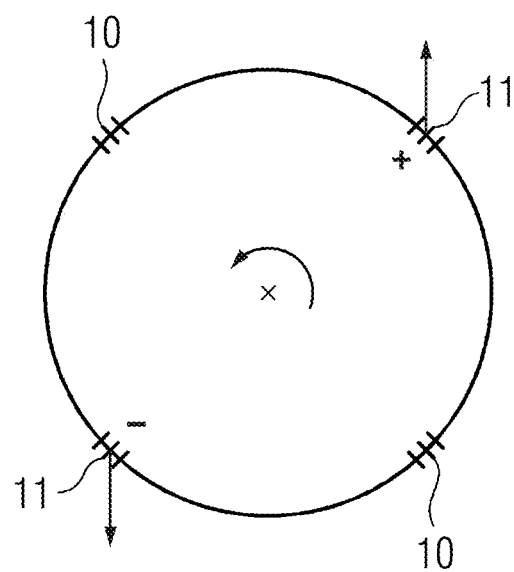
Figure 7:
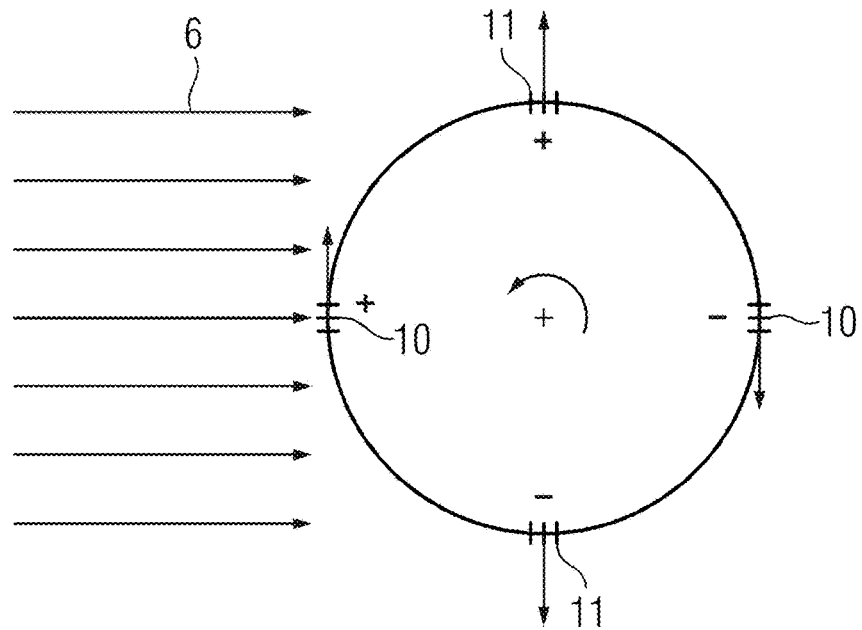
Figure 8:
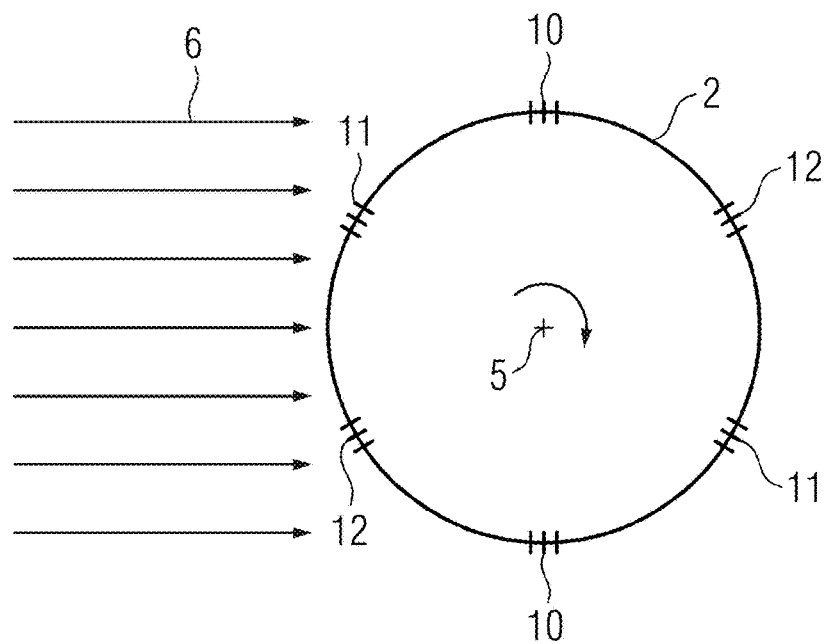
Figure 9:
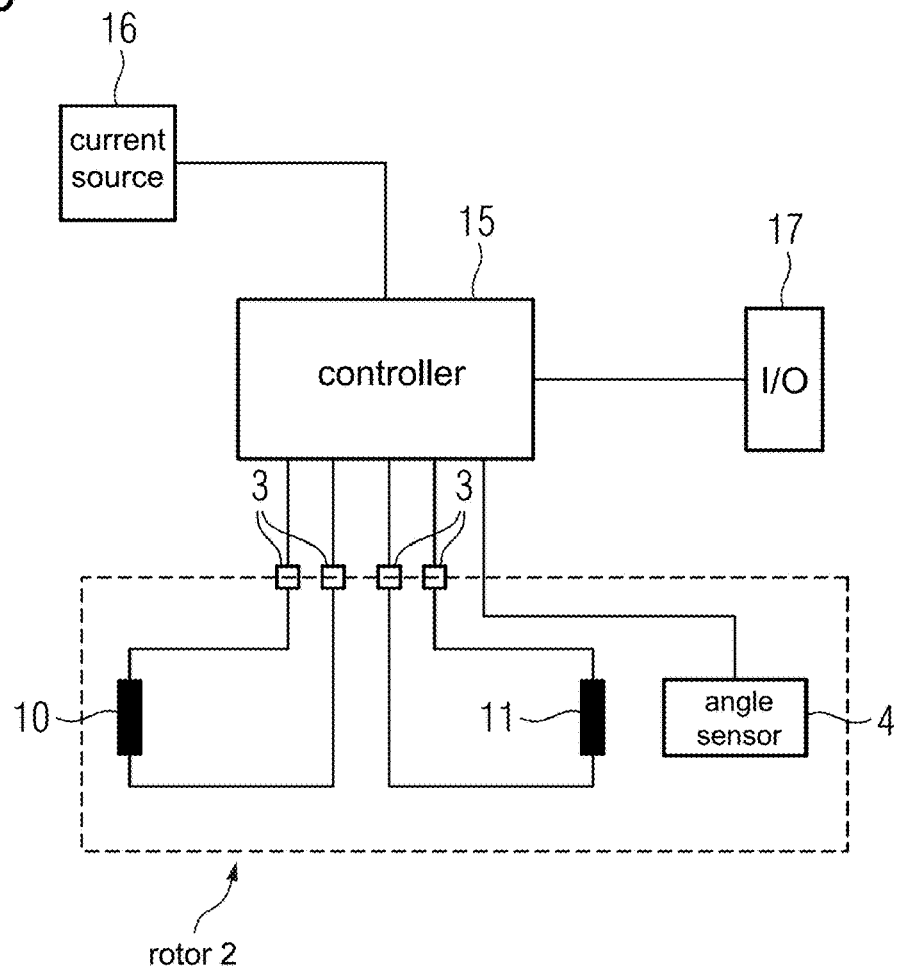
Figure 10:
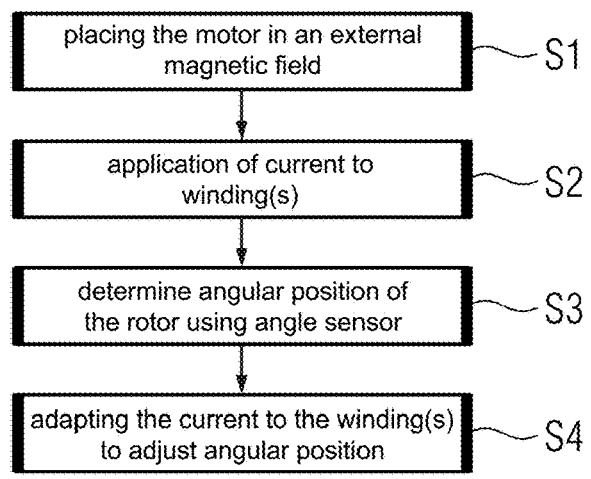

FIG. 1 is a perspective view of the motor according to an embodiment of the present disclosure, FIG. 2 is a perspective schematic view of a motor according to an embodiment of the present disclosure, FIG. 3 is a schematic sectional view of the rotor of a motor according to an embodiment of the present disclosure, FIG. 4 is a schematic sectional view of the rotor of FIG. 3 in an angular position, FIG. 5 is a schematic sectional view of the rotor of FIG. 3 in a further angular position, FIG. 6 is a schematic sectional view of the rotor of FIG. 3 in a further angular position, FIG. 7 is a schematic sectional view of the rotor of FIG. 3 in a further angular position, FIG. 8 is a schematic sectional view of a rotor of a motor according to an embodiment of the present disclosure, FIG. 9 is a schematic diagram of a motor with further components according to an embodiment of the present disclosure, and FIG. 10 shows a flow diagram of a method according to an embodiment of the present disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to provide a DC motor, for operation in an external magnetic field, which can generate a sufficiently large torque and is precisely controllable.

According to a first aspect of the present disclosure, a DC (direct current) motor is provided for operation in an external magnetic field, comprising a rotor which is rotatable about a rotation axis and has at least two windings, at least four continuous rotary transmitters, wherein two rotary transmitters are associated with each of the windings and are configured to supply the respectively associated winding with direct current, an angle sensor which is designed to determine the angular position of the rotor, and a controller which is designed to control the current feed to at least one of the windings dependent upon the angular position of the rotor, wherein the motor is oriented in relation to an external magnetic field during operation so that the rotation axis extends transversely to the external magnetic field.

Compared with conventional motors, the DC motor according to exemplary embodiments differs according to the present disclosure, in particular, in the continuous rotary transmitter, the angle sensor and the controller. By this means, the motor can be used in an external magnetic field and a previously specified or determined angular position of the rotor can be achieved highly accurately. Thus, an apparatus which is driven by the motor according to the disclosure can be driven and/or adjusted very precisely. For this purpose, the motor can be operated in a stepper motor mode or in a servomotor mode. In a stepper motor mode, the rotor can carry out a rotation, not continuously, but in individual steps (i.e. stepwise). A step size can determine the achievable accuracy of the motor. In the stepper motor mode, the torque can fall when the rotary speed increases. Preferably the rotor of the motor that is used in stepper motor mode has 9-60 windings and therefore a step size of 18° to 3°.

In a servomotor mode, the rotor can carry out a movement that is proportional to a control signal and can therefore be controllable steplessly. In the servomotor mode, the torque can be dynamically dependent upon the load.

By contrast with this, the motors of the prior art that are used in external magnetic fields can only be switched on and off without their target position (i.e. their rotary angle) being capable of being exactly defined or determined in advance.

The external magnetic field can be, for example, a $B_0$ magnetic field of a magnetic resonance (MR) tomography unit (scanner). The external magnetic field can thereby have continuously extending field lines. The external magnetic field can serve in the motor according to the disclosure as a stator magnetic field. Furthermore, a magnetic leakage field of an MR scanner can be used as the external magnetic field.

The rotor can be a cylindrical body which is rotatably mounted in a housing of the motor. The mounting can be a radial bearing, for example, a sliding bearing or a roller bearing. In the case of a sliding bearing, for example, a Teflon bearing can be provided in order to reduce the sliding friction. In the case of a roller bearing, a ball bearing or an industrial bearing can be used. Through the use of standardized bearings, the production of the motor rapidly, easily and at low cost can be ensured. In an exemplary embodiment, ceramic ball bearings made, for example, of zirconium oxide and/or of silicon nitride are provided. Thereby, the longevity of the bearings can be increased.

In addition, the rotor has windings which can have conductors for conducting electric current. The windings can also be referred to as coils. Each winding can be electrically insulated. For example, insulated conductors can be used as the windings. Each winding can consist of a plurality of conductors. A winding can extend substantially along the longitudinal direction of the rotor and can be wound a plurality of times round the rotor. If the rotor is a cylindrical body, a winding can extend along the height direction of the cylinder and at least partially over both cover surfaces. The windings can cross one another on the cover surfaces of the rotor. In addition, each winding can be connected at one of the cover surfaces of the rotor to the rotary transmitter associated with the winding. The windings can be held by holding elements which are provided on the circumferential surface of the rotor. For this purpose, the holding elements can each have an undercut so that the respective winding is accommodated and held therein. The rotor can have a plurality of holding elements at each of the longitudinal ends of the rotor so that a plurality of windings can be provided on the rotor. The holding elements can be arranged evenly distributed over the circumference of the rotor. In this way, a simple application of the windings on the rotor is possible. In addition, further windings can easily be added or windings can easily be exchanged. If two windings which are each formed from a conductor are provided, it is advantageous that each conductor is wound a plurality of times round the rotor along the longitudinal direction of the rotor (that is, along the rotation axis of the rotor). Thereby, the two windings can be arranged on the rotor so that they have an angular spacing of substantially 90° to one another.

The rotary transmitter can be configured to transfer current from an immovable component (power supply) to a rotating component (rotor). Rotary transmitters can also be configured as continuous sliprings. In the prior art, it is known that in DC motors, sliprings can simultaneously also act as commutators, so that—as is usual in DC motors—a repoling can take place mechanically. For this purpose, the sliprings are provided with interruptions (i.e. they are not continuous). Typically, the current is transferred in the slipring to the rotating rotor by means of carbon brushes. However, at a transition from one portion of the slipring to the next (i.e. in the repoling of the current), so-called brush sparking, which can lead to a negative influence on the imaging during operation of an MR scanner, can occur. Therefore, according to the disclosure, continuous rotary transmitters are provided. Herein, continuous can mean that no interruptions are provided on the rotary transmitter. Rather, the surfaces which move relative to one another (i.e. the stationary surface and the rotating surface) of the rotary transmitter are configured continuous, so that the mechanical pole change processes, as in the case of interrupted rotary transmitters, do not occur. Thereby, the occurrence of brush sparking can be prevented, so that it is ensured that the MR tomography imaging can operate without interference from the motor. Since no repoling takes place in a rotary transmitter, each winding is associated with two rotary transmitters. In other words, one of the two rotary transmitters can serve as a positive pole and the other rotary transmitters can serve as a negative pole of the associated winding. For this purpose, the rotary transmitter can be connected in series to the winding.

The angle sensor can determine the angular position of the rotor with the aid of an optical system, a mechanical/electrical system, a magnetic system or a combination of the systems mentioned. Thus, the angular position can be acquired, for example, with the aid of a potentiometer. In addition, the angular position can be determined with a magnetic system using Hall effect sensors. The angle sensor can also be designated an encoder or rotation sensor. In an exemplary embodiment, a purely optical measuring system is used in which by means of lightguide scanning of an encoder disk and subsequent screened signal evaluation, an angle change of the rotor can be determined. Independently of the system used, the angle sensor can output a voltage which corresponds to the angular position of the rotor. For this purpose, the encoder disk can be mounted on the rotor so that it rotates with the rotor. The angle sensor can be located on the shaft of the rotor. In an exemplary embodiment, the angle sensor is mounted on the same side in relation to the windings of the rotor as the rotary transmitter.

The controller can be configured to feed direct current to the windings individually and separately from one another via the rotary transmitter and to set variably the current direction of the direct current fed to the windings. The controller can be a circuit which can control the operation of the motor by controlling switches and other control devices. In addition, the controller can comprise a processor (e.g. CPU) for processing signals. The controller can accept signals (e.g. commands, measurement values, acquisition values, etc.) and output control signals. The controller can be configured to accept signals from the angle sensor (e.g. a voltage) and on the basis of these signals (i.e. on the basis of the angular position of the rotor) to control the current feed to the windings. Furthermore, the controller can be configured to accept signals (e.g. control signals, target position of the rotor, etc.) from an interface. In addition, the controller can be configured to compare the signals from the angle sensor with the signals from the interface and, on the basis of this comparison, to control the current feed to the windings. In addition, the controller can comprise a storage unit which can be configured to store an operating program and/or measurement values permanently or temporarily.

The angular position of the rotor can be expressed as a value in degrees. In addition, the angular position of the rotor can be a relative value or an absolute value. For example, a position of the rotor in which the first winding is horizontally oriented and the second winding is vertically oriented is designated a starting position (angular position of 0°). If the rotor then rotates, for example, about its rotation axis, so that a first winding is oriented vertically and the second winding is oriented horizontally, an angular change or an angular position of 90° has come about.

During an operation of the motor, the motor is oriented relative to an external magnetic field so that the rotation axis of the rotor extends transversely to the external magnetic field (i.e. to the field lines of the magnetic field). For an orientation of the rotation axis of the rotor transversely to the field lines of the magnetic field, it is sufficient that at least one component of the respective field lines extends orthogonally to the rotation axis, i.e. there must be a particular minimum field strength orthogonally to the rotation axis. In other words, with an orientation of the rotation axis transversely to the field lines, the rotation axis and the field lines include every angle, with the exception of 0° and 180°. In an exemplary embodiment, the angle lies between 30° and 150°, more preferably between 50° and 130° and still more preferably between 70° and 110°. This means that the rotation axis can be arranged so that it does not extend parallel to the field lines of the magnetic field. The field lines of the magnetic field can be resultant field lines of higher-order magnetic fields. In other words, smaller eddy currents can remain out of consideration provided at least one component of the respective field line extends substantially orthogonally to the rotation axis of the motor.

The motor can adjust a couch, for example, using a spindle, lead screw and/or a transmission apparatus. In particular, a headrest of the couch can be adjusted with the motor. In addition, the motor can adjust an inclination of the couch relative to the horizontal or, during an imaging process, bring about an advancing of the couch into an MR scanner. Furthermore, the height of the couch can be adjusted with the motor. Since no permanent magnet or similar is provided for the motor, it does not need to be ensured that the motor has a particular spacing from the MR magnet. Thus, an increased level of design freedom exists in the construction of the couch and the overall MR system. In addition, the operation of the couch is simplified overall since it does not have to be ensured that the couch does not approach the MR magnet too closely.

In addition, the motor can also be used in a calibration of an MR system. Thereby, motion control components can be calibrated and/or tested. For example, a dummy (i.e. a mannequin that simulates a real patient) can be moved in a realistic manner by the motor while the magnetic field is active in the bore and test scans can be carried out. Thus, a movement compensation can be calibrated. The movements can be carried out with the motor repeatably and in a predetermined manner, whereby the calibration can be simplified.

It is also conceivable that the motor is used when adjusting the MR system by means of shim devices in order to homogenize the magnetic field. Thus, for example, with the aid of the motor, a rotation of a measurement apparatus carried out manually in the prior art can be automated in the magnetic field so that the service technician no longer has to carry it out manually. In this way, a tune-up of the MR system can be accelerated, which leads to savings of cost and time.

A use of the motor in the calibration of Hall effect sensors is also conceivable. In the calibration of Hall effect sensors, it is necessary to move them in a particular manner in a predefined magnetic field. In this so-called elliptical fitting calibration, the motor can advantageously be used in order to move the Hall effect sensor to be calibrated in a defined manner, since the motor is operable without difficulty and highly accurately in external magnetic fields.

In an exemplary embodiment, the motor is made of plastics, ceramics and/or copper. In an exemplary embodiment, the motor contains no ferromagnetic materials. The motor can therefore be placed without difficulty (i.e. without corresponding anchoring) in a strong external magnetic field. Furthermore, the motor is also able to be manufactured economically since it is not necessary to use neodymium magnets as in a market-typical servomotor. In this way, costs can be saved in the production.

In an exemplary embodiment, each winding lies at least approximately in a plane with the rotation axis. In other words, each winding can lie in the same plane with the rotation axis. The rotor can have a plurality of windings which extend substantially along the longitudinal direction (that is, along the rotation axis) of the rotor. Each winding can extend on one side of the rotor from a terminal on the respective rotary transmitter parallel to the longitudinal direction of the rotor, then change over at the end of the rotor to the opposite side of the rotor and there extend back again parallel to the rotation axis of the rotor to the terminal. In other words, the conductor from which a winding can be made can be arranged opposite itself (that is in relation to the rotation axis of the motor). Substantially can mean, in this context, that the conductors forming the winding are not arranged exactly opposite, but are opposite with manufacturing tolerances. For example, these manufacturing tolerances can mean a deviation of approximately 5%. A plane can be defined in the present case by two straight lines extending at 90° to one another. In a plan view, each winding can have a substantially rectangular form. Additionally, each winding can surround the rotor peripherally. Thereby, the accessibility of the winding from outside can easily be ensured.

In an exemplary embodiment, a ratio between a diameter of the rotor and a length of the extent of the winding along the rotation axis of the rotor is less than 1, preferably less than 0.3. With this ratio, it is ensured that a Lorentz force generated acts on a sufficiently long length in order to generate a sufficiently large torque. Thus, a strong stepper motor can be provided. In addition, a ratio between the material used and the effect produced by the motor can be optimized with the defined ratio.

In an exemplary embodiment, the torque of the motor can be greater than 2.5 Newton meters. Thus, the motor can be configured, even without gearing by means of a gearbox, to be sufficiently powerful, for example, to move a couch of an MR system with a patient thereon horizontally and/or vertically without difficulty.

In an exemplary embodiment, each rotary transmitter has an electrically conductive and continuously extending first and second element. In an exemplary embodiment, the first element and the second element are arranged rotatable relative to one another. In an exemplary embodiment, during an operation of the motor, the second element rotates together with the rotor. In an exemplary embodiment, a gap is formed between the first element and the second element in which an electrically conductive liquid metal alloy, in particular a eutectic alloy which comprises gallium, indium and tin is arranged. The first element can have a first recess on its side facing toward the second element and the second element can have a second recess on its side facing toward the first element. An electrically conductive porous material can be arranged in the first and second recess. The liquid metal alloy can create an electrically conductive connection between the first element and the second element. The porous material can assist in holding the liquid metal alloy securely in the gap. The rotary transmitter can thus be configured to transfer an electric current from the first element to the second element regardless of whether the rotor is rotating or not. Current can thus be transferred from a stationary current source to the rotating rotor without a sliding contact, for example with carbon brushes, being necessary. As the rotary transmitter, for example, a rotary transmitter as described in EP 2498347 B1 can be used. The content of EP 2498347 B1 is also included herein by reference.

In an exemplary embodiment, the controller can be configured, on the basis of the angular position of the rotor, to short-circuit at least one winding, in particular, via a transistor cascade, so that a rotation of the rotor can be decelerated. In other words, if one of two windings is used to cause the rotor to rotate, the unused winding which also moves through the external magnetic field can be short-circuited. Due to the movement of the unused winding in the external magnetic field, a voltage is induced in this winding. A potential gradient can thereby be caused in the winding. If this winding is then short-circuited, which means that a current flow is caused in this winding in accordance with the induced potential, a Lorentz force acts against the rotation direction of the rotor and decelerates the rotor. The Lorentz force generated is dependent upon the rotary speed of the rotor before the short-circuit and becomes zero when the rotor no longer moves in an external magnetic field. In other words, the decelerating effect caused can be proportional to the rotary speed of the rotor. It can thus be ensured at any time that, by short-circuiting an unused winding, a sufficiently great decelerating effect is generated in order to stop the rotor in the desired position. The short-circuiting of the unused winding can be brought about by a switch. Short-circuit can mean, in accordance with the disclosure, that a current circuit is closed so that a current can flow substantially without additional resistors (for example, consumers or suchlike). The rotor can thus be brought into rotation by one winding and decelerated by the other winding. If the rotor has reached its desired position, the winding previously used for the rotation (i.e. the winding supplied with current) can be powered again in order to increase a holding torque of the motor in the desired position. The winding further supplied with current in this way brings about a radial force component due to the Lorentz force, which is unable to bring the rotor into rotation. Thus, the rotor can be held in the desired position and a holding torque can be increased.

Deceleration can be carried out with more than just one winding, and thus a plurality of windings can be provided in the motor, wherein with a particular number of windings, the rotor can be accelerated and with a particular number of windings, the rotor can be decelerated. In an exemplary embodiment, deceleration takes place with the same number of windings as previously were used for acceleration.

In order to limit the current flowing during the short-circuit, at least one transistor can be provided which can limit the current so that the decelerating effect and/or the deceleration force can be limited. The transistor can also be a controlled transistor, so that the current flowing during a short-circuit of a winding can be actively controlled by the controller. Thus, the circuit and the motor can be protected against damage. The decelerating effect can be generated, in particular, as a result of eddy currents that are generated during the short-circuit. In an exemplary embodiment, the controller can short-circuit at least one winding at a particular time (i.e. at a particular angular position of the rotor) on the basis of the information items it receives from the angle sensor. By means of the short-circuit, the rotor can be strongly decelerated and can immediately come to a standstill. It can be ensured thereby that the rotor does not oscillate about the target position, but assumes the target position directly. After a 180° rotation of the rotor, the current direction to the windings used for driving can be reverse-poled in order to rotate the rotor further in the same direction.

The deceleration can be used, in particular, during an operation of the motor in a stepper motor mode. In the stepper motor mode, a single step that is carried out by the motor can be dependent upon the number of windings. A step can be defined such that it has an angular spacing from one winding to the adjacent winding. Thus, if two windings are provided, one step can be 90°. If three windings are provided, one step can be 60°. If four windings are provided, one step can be 45°, and so on. For highly accurate stepper motors, for example, a step size of 1.8° can be set. In this case, 100 windings can be provided on the rotor. In an exemplary embodiment, however, 8 to 10 windings are provided, so that a step size of 22.5° to 18° can result. In stepper motor mode, the controller can control the application of current to the windings so that the rotor rotates stepwise by the angular spacing between two adjacent windings.

For controlling the application of current to the windings, the controller can have a bridge circuit, also called an H-bridge or a full bridge. It is therefore advantageously possible to change the current direction by controlling the switches in the bridge circuit. MOSFET switches, transistors, IGBT transistors or relays can be used as switches. In other words, the controller can switch the current flow to each winding on and off and can change the direction of the current that is applied to each winding. In addition, the controller can be configured to change (i.e. set) the voltage that is applied to each winding. In this way, the rotation direction and the torque of the motor can be controlled.

In an exemplary embodiment, the rotor can comprise three windings which are arranged on the rotor. The three windings can be arranged evenly distributed in the circumferential direction of the rotor. In other words, the three windings can have an angular spacing of 60° from one another. In addition, more windings can also be arranged on the rotor, and can be arranged evenly distributed in the circumferential direction of the rotor. If the rotor has three windings, the motor can be operated in a servomotor mode. In that regard, a target angular position that the motor is to assume during an operation can be preset (for example, via the interface). In that regard, the position of the rotor can be determined continuously by means of the angle sensor. For this purpose, the angle sensor can output, for example, a voltage which corresponds to the current angular position. The target position can also be expressed as a voltage. In addition, a comparator can be provided which compares the output of the angle sensor with the voltage of the specified target position and drives the motor until the two voltages match, i.e. the rotor has reached the desired position. During an operation of the motor in the servomotor mode, at least two of three windings can be supplied with current simultaneously. The two windings simultaneously supplied with current can have a mutually contrary current flow. In this way, it can be ensured that a Lorentz force that is generated brings about a rotation of the rotor in the same direction so that the rotor is brought into movement. In addition, the current strength in the windings can be set so that the rotor can reach the desired position (i.e. the target position). In other words, the current strength in the individual windings can be varied dependent upon the position of the windings (i.e. dependent upon the position of the rotor). This is particularly advantageous in order to bring about an even rotation of the rotor, since a winding can be oriented to the magnetic field such that the Lorentz force created in this winding provides only a radial force component to the rotor and this therefore makes no contribution to a rotation of the rotor. In other words, there is an angular position of the rotor in which a winding can create no tangential force component (due to the Lorentz force) that contributes to the rotation of the rotor. This angular position can be present when a winding lies, together with the rotation axis, in one plane and the field lines of the external magnetic field extend parallel to the plane (this position can also be designated the dead point). In contrast thereto, the at least two further windings can each generate a tangential force component, each of which can make a contribution to a rotation of the rotor. In addition, the application of current to the windings in a servomotor mode can be controlled so that the rotor becomes slower before reaching the target position. It can thus be prevented that the rotor oscillates about the target position and/or overshoots the target position. In an exemplary embodiment, the application of current to the windings can be controlled by the controller such that the rotor is accelerated rapidly and then becomes slower the nearer it approaches to its target position. Alternatively or additionally, the controller can decelerate the rotation of the rotor in that one of the windings is short-circuited and/or a Lorentz force counteracting the rotation is brought to bear (i.e. by short-circuiting one winding or by targeted application of current to one winding).

In an exemplary embodiment, the controller can be configured to control the current feed to the windings by means of a vector control system. The current feed can comprise a current strength in the present case. In addition, the current feed can also comprise the current direction. The forces generated in each winding can be brought together with the aid of the vector control and a resultant force component can be determined. The current strength and the current direction which can be applied individually to each winding can be set such that the resultant force components bring the rotor into rotation in the predetermined direction and with a predetermined torque. In other words, the vector control can denote a determination of the resultant force vector and can therefore be controlled so that the target position can be reached as quickly as possible and highly accurately.

In an exemplary embodiment, the angle sensor can be an optical system which is configured to acquire the angular position of the rotor by scanning a pole wheel. A pole wheel can rotate together with the rotor during an operation of the motor. The pole wheel can have markings (e.g. cut-outs and/or elevations) that can be acquired by an optical system. The markings can correspond to an increment or an acquisition step, so that the more increments that are provided, the more an acquisition accuracy of the angular position can be increased. Thus, on the basis of the markings acquired (i.e. on the basis of the number of markings acquired or the type of the markings acquired), the angle sensor can output a current angular position of the rotor. In an exemplary embodiment, the pole wheel has twice as many markings as the rotor has windings. In an exemplary embodiment, the pole wheel can be configured so that the angle sensor can resolve in the range of 800 to 1500 steps, preferably in a range of 900 to 1200 steps and particularly preferably 1000 steps. For this purpose, the pole wheel can have a corresponding number of markings. Such a high resolution is advantageous, in particular, for the servomotor mode. In an exemplary embodiment, the controller can control the motor with a closed-loop control system on the basis of the information items acquired by the angle sensor, in particular, in servomotor mode. Thereby, an optimum ratio between manufacturing costs and control accuracy can be achieved. The angle sensor can be designed, for example, as a light-barrier system which can determine the number of interruptions of a light beam by the pole wheel. On the basis of the interruptions, it can be determined in which angular position the rotor is situated. The pole wheel can also be referred to as an encoder disk.

The motor can thus be used in an external magnetic field as a stepper motor or as a servomotor, whereas the DC motors known from the prior art are not configured to operate in the magnetic field of an MR scanner as a stepper motor or as a servomotor.

According to a further aspect of the present disclosure, a couch of an MR system is provided, comprising a DC motor, wherein the couch is adjustable and/or displaceable by means of the DC motor. The couch can be formed, for example, from a patient table on which a patient is able to be placed, and a substructure which is, for example, movable. The patient table can be movable relative to the substructure. The patient table can be displaced continuously, for example, with the aid of the motor, relative to the substructure in different directions (e.g. in the horizontal and/or the vertical direction). Such a couch can be used, for example, during an imaging process by means of MR tomography. Therein, a patient can be situated on the patient table of the couch and through the movement of the patient table, can be brought into an image plane intended for the imaging in a bore of an MR scanner. Therein, the couch can also be situated, at least partially, in the bore. A magnetic field with a strength of approximately 0.5 tesla to 11 tesla can prevail in the bore. In addition, the patient table of the couch can be also adjusted in its height direction with a DC motor, in particular, relative to the substructure, so that the patient can be moved into the imaging planes of the MR scanner. In addition, the patient table can also be adjusted in sections by the DC motor, and thereby for example, a headrest or another part of the patient table can be tilted, inclined or displaced in its position in order to offer the greatest possible comfort to the patient and simultaneously to position the patient optimally in the image plane of an MR scanner.

According to a further aspect of the present disclosure, a method for operating a DC motor in an external magnetic field is provided, wherein the motor has a rotor that is rotatable about a rotation axis and has at least two windings, at least four continuous rotary transmitters, wherein two rotary transmitters are associated with each of the windings and are configured to supply the respectively associated winding with direct current, and has an angle sensor which is designed to determine the angular position of the rotor, the method comprising the following steps: placing the motor in an externally generated magnetic field, in particular, in a magnetic field of a magnetic resonance scanner, so that the rotation axis of the motor extends transversely to the field lines of the magnetic field, applying current to at least one of the windings so that the rotor rotates about the rotation axis, in particular, due to a Lorentz force generated thereby, determining the current angular position of the rotor using the angle sensor, adapting the application of current to the windings so that the rotor assumes a predetermined angular position. The placement of the motor can be realized, for example, in that the motor is fastened to a couch which can be used to bring a patient into the bore of an MR scanner and to support him there. It is therein necessary only to place the motor so that the field lines of the magnetic field of the MR scanner extend transversely to the rotation axis of the rotor. It does not have to be ensured that the motor does not come too close to the MR magnet as in the prior art. Thus, the motor can be mounted at positions favorable for the functioning of the motor and for the production of the couch. In other words, care need only be taken over the orientation of the motor and no longer over the location of the placement. Thereby, the freedom of design of the couch and of an MR system altogether can be enhanced. In other uses of the motor in an external magnetic field, the motor can be oriented, for example, manually so that field lines of the external magnetic field extend transversely to the rotor axis. Otherwise, it is conceivable that the motor is automatically oriented by an orientation apparatus. Therein, the field lines can be measured and, on the basis of the measurement result (i.e. the direction of the field lines of the magnetic field), the motor can be oriented automatically such that the field lines extend transversely to the rotation axis. For example, the motor can be used according to one of the above embodiments in the method.

Adapting the application of current can comprise the selective powering of one or more windings. Thus, a winding can be supplied with current in order to cause the rotor to rotate. Therein, exactly the one winding or plurality of windings, which can exert a tangential force component on the rotor due to the Lorentz force, can be supplied with current. The position of the windings in an external magnetic field can be acquired by the angle sensor. Therein, the orientation of the field lines is known and preset or measured in parallel by the field line measuring device (e.g. with one or more Hall effect sensors).

In addition, an adaptation of the application of current can comprise an interruption of the application of current to one or more windings. Thus, shortly before achieving a target position of the rotor, an application of current to one or more windings can be interrupted, so that the rotation of the rotor is slowed (e.g. due to the friction and/or a load). Furthermore, adaptation of the application of current can also comprise an implementation of a particular current direction in at least one of the windings, so that a force component counteracting the rotation is generated. Finally, the adaptation of the application of current can also comprise a short-circuiting of at least one of the windings, so that a previously induced voltage leads to a current flow, which itself brings about a Lorentz force counteracting the rotation. In this way, the rotor can be brought to a standstill with precision. The adaptation can be carried out by means of a controller with the aforementioned features.

In an exemplary embodiment, the step of adapting the application of current can comprise a short-circuiting of at least one of the windings or an adaptation of the current strength in the windings. Herein, the short-circuiting in a motor with two windings can be carried out in a stepper motor mode. The adaptation of the current strength in the windings can take place in a motor with at least three windings in a servomotor mode.

In the stepper motor mode, the rotor can have at least two windings. The movement interval (i.e. the step size) of the motor can correspond to the angular spacing between two windings. This means that the more windings are provided, the smaller are the movement intervals of the rotor. In a stepper motor mode, at least one winding which provides for the movement of the rotor can be supplied with current. The unused winding can be short-circuited on reaching the target position, so that the rotor comes to a standstill. If a plurality of windings is present, the winding adjoining the dead point can be supplied with current in order to cause the rotor to rotate. The dead point is the point (angular position) and/or the position of the rotor at which an application of current to the winding situated there leads only to a radial force component and thus makes no contribution to a rotation of the rotor. The winding not used for the application of current, which is short-circuited in order to stop the rotor, can be at any desired position (i.e. only not at the dead point). However, since the dead point can be the target position of the winding to which current is to be applied, this requirement is automatically fulfilled in this case.

In a servomotor mode, three windings are preferably provided on the rotor so that the rotor can rotate continuously in the desired direction, dependent upon the current direction in the respective winding. For example, a winding can be situated at the dead point and therefore cannot be used for accelerating the rotor. Therein, the windings can be supplied with current until the target position is reached. During a movement of the rotor, a repoling of the application of current can become necessary so that the rotor further rotates in one direction. In contrast to the stepper motor mode, on reaching the target position in the servomotor mode, none of the windings can be at the dead point. Therefore any desired target positions can be adopted by means of a continuous movement. Optionally, in the servomotor mode, a deceleration can be carried out using the unused winding, in order to brake the rotor in the target position.

In an exemplary embodiment, the motor can be used in an MR system. Furthermore, the motor can also be used in production, wherein the motor can be used in a calibration of Hall effect sensors and in testing of motion-control components (enablers) of magnetic resonance scanners.

Otherwise, the same embodiments and advantages apply to the method as for the apparatus, and vice versa.

FIG. 1 shows a perspective schematic view of a motor according to an embodiment of the present disclosure. The motor 1 has a rotor 2 which is rotatable about a rotation axis 5. The rotor 2 has three windings 10, 11, which extend substantially along the rotation axis 5 on the rotor 2. In addition, the motor 1 has four rotary transmitters 3, of which two rotary transmitters 3 are associated with each of the windings 10, 11. This means that one rotary transmitter 3 represents the positive pole of the first winding 10 and the other rotary transmitter 3 represents the negative pole of the first winding 10. In exactly the same way, one rotary transmitter 3 represents the positive pole of the second winding 11 and a further rotary transmitter 3 represents the negative pole of the second winding 11. Thus, two rotary transmitters 3 are connected in series with one of the windings 10, 11 in each case. The rotary transmitters 3 can have current applied to them controllably by means of a controller 15. The rotary transmitters 3 then transmit the current to the winding 10, 11 associated with the rotary transmitters 3. Thus, the controller 15 is configured to control the current feed to at least one of the windings 10, 11. In addition, the controller 15 can set the current direction to the windings 10, 11 individually for each winding. In an exemplary embodiment, the controller 15 includes processing circuitry that is configured to perform one or more functions of the controller 15, including, controlling the current feed to at least one of the windings, controlling the current direction, and/or otherwise controlling the motor 1.

Furthermore, the motor has an angle sensor 4 which is configured to determine the angular position of the rotor 2. The angular position is the position of the rotor expressed as an angle about its rotation axis 5. The angular position can be a relative size or an absolute size. The angle sensor 4 is arranged, in relation to the rotor 2, on the same axial side of the motor 1 as the rotary transmitters 3. In this way, an optimized cable routing can be provided since a common cable routing can be fed to the angle sensor 4 and to the rotary transmitter 3. In an alternative embodiment (not shown), the angle sensor is arranged, in relation to the rotor 2, on the same axial side of the motor 1 as the rotary transmitters 3. The angle sensor 4 is therein wirelessly connected to the controller 15. In an exemplary embodiment, the angle sensor 4 includes processing circuitry that is configured to perform one or more functions of the angle sensor 4.

In addition, the rotor 2 has holding apparatuses 7 which are arranged distributed evenly over the circumference of the rotor 2 and are configured to hold the windings 10, 11 in a particular position. Therein, the holding apparatuses 7 are configured so that they can hold the windings 10, 11 in place reliably even at relatively high rotary speeds and/or high accelerations. For this purpose, the holding apparatuses 7 have undercuts in which the windings 10, 11 are held. In addition, the motor 1 has a housing (not shown in FIG. 1) in which the components of the motor 1 are accommodated. In addition, the terminals of the rotary transmitters 3 and of the angle sensor are all arranged on the same side of the motor 1. Thus, an optimized cable routing can be ensured and the motor 1 can be compactly constructed.

The rotor 2 in the present embodiment is a cylindrical body with a surface shell and two cover surfaces. The rotor 2 is rotationally symmetrical in relation to the rotation axis 5. In an alternative embodiment (not shown), in section the rotor 2 is a polyhedron with twice as many faces as windings.

The windings 10, 11 are insulated conductors which become windings 10, 11 by winding round the rotor 2 multiple times along the rotation axis 5 of the rotor 2. The conductor of each winding 10, 11 is connected at one end to one rotary transmitter 3 and at the other end to another rotary transmitter 3. The conductors cross one another at the cover side of the rotor. The rotary transmitters can also be configured as sliding contacts.

FIG. 2 shows a schematic perspective representation of the motor 1 wherein for the sake of simplifying the description, individual components are omitted. Shown in FIG. 2 is the external magnetic field 6. In the present embodiment, the external magnetic field 6 is a magnetic field of a magnetic resonance scanner (the $B_0$ field) and extends constantly with substantially parallel field lines (see arrows in the figure). The external magnetic field can have a strength from 0.5 to 11 tesla. In FIG. 2 the rotation axis 5 is also shown dot-dashed. In FIG. 2, the rotor 2 is oriented so that the first winding 10 is situated in a dead point. A winding is situated in a dead point if an application of current to the windings would only evoke a force component extending radially to the rotor 2 and therefore cannot cause the rotor 2 to move. In other words, in the example shown in FIG. 2, an application of current to the first winding 10 would bring about no movement of the rotor.

If, however, in FIG. 2 the winding 11 is supplied with current, i.e. is connected to an energy source such that current flows through the winding 11, a tangential force component acts due to the Lorentz force on the rotor 2. These tangential force components cause the rotor 2 to rotate in the clockwise direction in the present embodiment. If, however, the first winding 10 is supplied with current as shown in FIG. 2, then a radial force component acts on the first winding 10 and therefore on the rotor 2, and makes no contribution to a rotation of the rotor 2. In other words, the rotor 2 can only be brought into rotation if the Lorentz force generated has a tangential force component in relation to the rotor 2.

A rotary direction of the rotor 2 can be altered with an alteration of the current direction. A controller 15 is provided and is configured to adapt the current direction of the current flowing through the windings 10, 11. Thus, the rotor 2 can be rotated into the desired direction.

FIG. 3 shows schematically a section through the rotor of FIG. 2. In contrast to the position of the rotor 2 in FIG. 2, the rotor 2 shown in FIG. 3 has rotated by 90° counterclockwise. In this case, the first winding 10 is situated in the dead point so that the first winding 10, on application of current thereto, only generates a radial force component and therefore cannot cause the rotor 2 to rotate. If, however, the second winding 11 is supplied with current (i.e. it is connected to a current source), the rotor 2 is caused to rotate. When the second winding 11 then reaches a vertical position (in FIG. 3, the up/down direction, i.e. the dead point), the application of current to the second winding 11 also contributes no force component that could cause the rotor 2 to rotate. The rotor 2 would oscillate somewhat back and forth and then come to a standstill with the second winding 11 oriented vertically. This oscillation movement is undesirable in an operation of the motor 1 as a stepper motor. Therefore, the controller 15 controls the current feed to the windings 10, 11 so that, in particular, the back and forth oscillation of the rotor 2 is prevented. Herein, the controller 15 short-circuits the winding not used for the movement (that is, not supplied with current). Thus, the predetermined angular position is reached reliably and exactly (that is, without the oscillation movement described above). Details thereof are set out by reference to FIG. 4.

FIGS. 4 to 7 show four schematic sectional views of the rotor 2 of FIG. 3 in different operating positions. In FIG. 4, none of the windings 10, 11 is connected to the current source and the rotor 2 stands still. The external magnetic field 6 acts in the side views shown in FIGS. 4 to 7 always from left to right (for clarity, shown with arrows only in FIG. 4).

In FIG. 5, current is applied to the second winding 11 (i.e. it is connected to a current source). In the figure, the right side of the winding 11 has a positive polarity and the side of the winding 11 shown on the left has a negative polarity. Accordingly, given a current flow through the second winding 11, the Lorentz force tangentially to the rotor 2 is as shown by the arrow in FIG. 5. Consequently, the rotor 2 rotates contrary to the clockwise direction.

In FIG. 6, the rotor 2 rotates contrary to the clockwise direction and therefore also displaces the windings 10, 11. In accordance with the displacement on the circular path of the rotor 2, the tangential force component which makes a contribution to the rotation of the rotor 2 becomes smaller until it reaches 0 when the second winding 11 has reached the vertical orientation (i.e. the dead point). The controller 15 has acquired or preset as a predetermined angular position, a position of the rotor 2 in which the second winding 11 is oriented vertically. In the present embodiment, this corresponds to a step in the stepper motor mode. The controller 15 continuously records the current angular positions of the rotor 2 by means of the angle sensor 4.

In FIG. 7, the rotor 2 has reached the desired and predetermined target position. In order to stop the rotor 2 in this predetermined target position (i.e. in order to prevent a back and forth oscillation), the controller 15 short-circuits the first winding 10 by closing a switch, so that the voltage induced by the movement of the winding 10 through the magnetic field 6 brings about a current flow which, in turn, brings about a tangential Lorentz force contrary to the rotation direction of the rotor 2. By this means, the rotor 2 is decelerated suddenly, since the Lorentz force acting (that is, the deceleration force) of the first winding 10 is dependent upon the speed with which the first winding 10 has been moved through the magnetic field 6. If the rotor 2 comes to a stop, a potential gradient no longer exists in the second winding 10, whereby no more current flows through the second winding 10 and therefore no Lorentz force acts. Consequently, the rotor comes to a stop exactly at the target position. In some embodiments, the second winding 11 is still supplied with current, even when it is already in the target position (in the vertical orientation in the embodiment shown in FIG. 7). Thereby, a holding torque of the motor 1 can be generated and the rotor 2 can be held in the target position. In the embodiment shown, the step size is 90°. In embodiments that are also not shown, the rotor 2 has ten windings and therefore has a step size of 18°.

The controller 15 controls the application of current, so that a winding that is provided adjacent to or abutting the dead point drifts into the dead point due to the movement. If a rotation of the rotor 2 is to be carried out that is greater than the size of a step, then a plurality of steps are carried out in succession.

FIG. 8 shows a further embodiment of the present disclosure. FIG. 8 is a schematic sectional view through a rotor 2 of a motor 1 according to a further embodiment of the present disclosure. The present embodiment has a third winding 12 on the rotor 2. The windings 10, 11, 12 are evenly arranged round the circumference of the rotor 2. In other words, the three windings 10, 11, 12 have an angular spacing of 60° from one another. In the present embodiment, at least two of the three windings 10, 11, 12 are supplied with current (that is, connected to the current source) so that a tangential force component of the Lorentz force of one of the windings 10, 11, 12 supplied with current can always be generated such that the rotor can move without difficulty into a predetermined angular position.

In the present embodiment, the motor 1 can be operated in a servomotor mode. Therein, the motor 1 is controlled so that it assumes any desired angular position. The rotor 2 does not move stepwise, but continuously or progressively. For this purpose, in the present embodiment, a further winding 12 is provided so that always two windings can apply a tangential force component to the rotor 2 and one winding can be used, for example, to decelerate the rotor 2. Thus, in the present embodiment, the motor 1 can be operated in the servomotor mode for precise positioning tasks.

The controller 15 can therefore control the motor 1 of the present embodiment with the aid of the vector control dependent upon the acquired position from the angle sensor 4 such that the predetermined angular position of the rotor 2 is reached. In the present embodiment also, an unused winding 10, 11, 12 can be used to bring the rotor 2 to a standstill at a desired position. A corresponding brake functions as in the previously described embodiment.

In a further embodiment (not shown), a plurality of windings (preferably 8-10 windings) is provided. Thus, primarily, a sufficiently strong motor 1 can be achieved. Thereby, the highest expectations can be placed on the accuracy and the strength of the motor 1 for operation as a servomotor for use in an external magnetic field. Thus the motor 1 of the present embodiment has a torque of at least 2.5 Nm.

FIG. 9 shows a schematic diagram which represents the motor 1 with further components. As mentioned above, the controller 15 can control the current feed from a current source 16 to the windings 10, 11. The current source 16 can be a current store such as a battery or an accumulator or the power network. Furthermore, the current is fed to the windings 10, 11 as described above via rotary transmitters 3. The controller 15 can accept signals from the angle sensor 4. For this purpose, the angle sensor 4 can be connected by a cable or wirelessly to the controller 15. The angle sensor 4 outputs a voltage which corresponds to the position of the rotor. The controller 15 can associate an angular position with the voltage. The controller can output the angular position of the rotor 2 or use it for other processes. An interface 17 is also provided which is an interface either with a user or with a further system (computer system). By means of the interface 17, the controller acquires the commands for operating the motor 1 and can output information regarding operating states of the motor 1. In particular, the controller obtains the target position of the rotor 2 via the interface 17.

In stepper motor mode, the controller 15 assigns to the target position a particular number of steps to be carried out (dependent upon the step size) and a rotation direction of the rotor 2. On the basis thereof, the controller controls the application of current to the windings 10, 11. Herein, the angle sensor 4 is used to carry out the individual steps precisely (in particular the above described deceleration intervention).

In the servomotor mode, the controller 15 assigns to the received target position a particular target voltage and compares it with the current angular position (i.e. with the voltage output by the angle sensor). This can be carried out with the aid of a comparator. Then the controller 15 drives the rotor 2 until both voltages substantially match, i.e. until the rotor 2 has reached the target position.

FIG. 10 is a schematic flow diagram of a method according to the disclosure for operating a DC motor 1 in an external magnetic field 6. In the method, a motor 1 according to one of the above embodiments can be used. The method has a step of placing S1 the motor in an external magnetic field. The motor 1 is positioned in the external magnetic field 6 so that the rotation axis 5 is oriented transversely to the field lines 6 of the magnetic field. In one embodiment of the present disclosure, the motor 1 is provided in a couch of an MR system and is oriented there accordingly so that if the couch is in an operational state in or on the MR system, the motor is held so that the rotation axis 5 of the motor 1 extends transversely to the field lines 6 of the magnetic field.

In addition, the method includes an application of current S2 to at least one of the windings 10, 11, 12 so that the rotor 2 rotates about the rotation axis 5. As previously described in the embodiments above, by means of targeted application of current (i.e. a connection of at least one of the windings 10, 11, 12) with a current source, a tangential force component is generated which can cause the rotor 2 to rotate about the rotation axis 5. At the same time or subsequently, in a step of determining S3, the current angular position of the rotor 2 is determined using the angle sensor 4. With the knowledge of the angular position of the rotor 2 and thus also of the positions of the windings 10, 11, 12, the corresponding winding 10, 11, 12 which can exert a desired (for example, the greatest) tangential force on the rotor 2 can be supplied with current. In addition, with knowledge of the exact angular position of the rotor 2 including during a deceleration process or immediately before reaching a predetermined target position, it is possible to determine the winding 10, 11, 12 which will be used to decelerate the rotor 2.

In addition, the method according to the disclosure comprises a step of adapting S4 the application of current to the windings 10, 11, 12 so that the rotor 2 assumes a predetermined angular position. For this purpose, the step of adapting S4 the application of current can comprise a short-circuiting of at least one of the windings 10, 11, 12 or of adapting the current strength in the windings 10, 11, 12. In other words, for example, in a motor 1 in which two windings 10, 11 are provided, one winding which is currently not being used for driving the rotor 2 is short-circuited in order to generate a Lorentz force acting against the rotation direction so that the rotor is decelerated abruptly.

In one embodiment in which the rotor 3 has a plurality of windings (for example 3), the current strength in the respective windings 10, 11, 12 can be controlled such that a resultant tangential force that acts on the rotor 2 has a desired size and/or direction. For this purpose, the windings 10, 11, 12 can also be switched rapidly one after the other in order, for example, to pass through a dead point in which a winding exerts only a radial force on the rotor 2. It should be noted that during a rotation, after 180°, the poling must be changed so that the force generated in the windings (i.e. the Lorentz force generated) continues to point in the already prevailing rotation direction. Such a change of the polarity can be realized, for example, by means of a bridge circuit. However, any other circuit which can change the positive and negative pole of a winding 10, 11, 12 is also suitable. In the present embodiments, the motor 1 is made of materials such as ceramics, plastics and/or copper.

The motor 1 according to the disclosure is used in one embodiment for calibrating Hall effect sensors. In particular, it can be used in this context for an "elliptical fitting calibration". Therein, the motor 1 can move a Hall effect sensor to be calibrated according to the circumstances in an existing magnetic field, so that correction parameters on the basis of the known limit conditions can easily be set.

In a further embodiment, the motor 1 according to the disclosure is used to calibrate a motion correction of an MR tomography system. Therein, a dummy (i.e. a mannequin) is introduced into an MR system and is moved by a motor 1 according to the disclosure. The movements can reproduce the real movements of a patient. Meanwhile, the image planes can be adapted on the basis of the known movements of the motor 1 so that the movements can be calculated out in a later imaging method.

In a further embodiment, the motor 1 according to the disclosure can be used during a measurement of a magnetic field, for example, in the bore of an MR system. Therein, the motor 1 can replace the otherwise manually performed movements and/or measurements at predetermined measurements in the bore. By this means, an automation and simplification of the tune-up of an MR system can be provided.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein. In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A direct current (DC) motor for operation in an external magnetic field, comprising:
   a rotor which is rotatable about a rotation axis and has first and second windings;
   at least four continuous rotary transmitters, wherein:
      first and second rotary transmitters of the at least four continuous rotary transmitters are associated with the first winding and are configured to supply the first winding with direct current, the first rotary transmitter forming a positive pole of the first winding and the second rotary transmitter forming a negative pole of the first winding, and
      third and fourth rotary transmitters of the at least four continuous rotary transmitters are associated with the second winding and are configured to supply the second winding with direct current, the third rotary transmitter forming a positive pole of the second winding and the fourth rotary transmitter forming a negative pole of the second winding;
   an angle sensor configured to determine an angular position of the rotor, and
   a controller configured to control the direct current feed to at least one of the first and second windings based on the angular position of the rotor,
   wherein the motor is oriented relative to the external magnetic field during operation such that the rotation axis extends transversely to the external magnetic field.

2. The DC motor as claimed in claim 1, wherein the first and the second windings lie in a plane with the rotation axis.

3. The DC motor as claimed in claim 1, wherein a ratio between a diameter of the rotor and a length of an extent of the first and the second windings along the rotation axis of the rotor is less than 1.

4. The DC motor as claimed in claim 1, wherein a ratio between a diameter of the rotor and a length of an extent of the first and the second windings along the rotation axis of the rotor is less than 0.3.

5. The DC motor as claimed in claim 1, wherein the angle sensor is an optical system configured to scan a pole wheel to acquire the angular position of the rotor.

6. The DC motor as claimed in claim 1, wherein:
   each of the at least four continuous rotary transmitters has an electrically conductive and continuously extending first and second element, the first element and the second element being arranged rotatable relative to one another,
   during an operation of the motor, the second element rotates together with the rotor, and
   a gap is formed between the first element and the second element in which an electrically conductive liquid metal alloy is arranged.

7. The DC motor as claimed in claim 6, wherein the electrically conductive liquid metal alloy is an eutectic alloy including gallium, indium and tin.

8. The DC motor as claimed in claim 1, wherein the controller is configured, based on the angular position of the rotor, to short-circuit at least one of the first and the second windings to decelerate a rotation of the rotor.

9. The DC motor as claimed in claim 8, wherein the controller is configured to short-circuit the at least one of the first and the second windings via a transistor cascade.

10. The DC motor as claimed in claim 1, wherein the rotor further comprises a third winding arranged on the rotor.

11. The DC motor as claimed in claim 10, wherein the controller is configured to control the current feed to the first, the second, and the third windings using a vector control system.

12. The DC motor as claimed in claim 1, wherein:
   the first rotary transmitter and the second rotary transmitter are connected in series; or
   the third rotary transmitter and the fourth rotary transmitter are connected in series.

13. The DC motor as claimed in claim 12, wherein:
   the first rotary transmitter and the second rotary transmitter are connected in series via the first winding; or
   the third rotary transmitter and the fourth rotary transmitter are connected in series via the second winding.

14. The DC motor as claimed in claim 1, wherein:
   the first rotary transmitter and the second rotary transmitter are connected in series; and
   the third rotary transmitter and the fourth rotary transmitter are connected in series.

15. The DC motor as claimed in claim 14, wherein:
   the first rotary transmitter and the second rotary transmitter are connected in series via the first winding; and
   the third rotary transmitter and the fourth rotary transmitter are connected in series via the second winding.

16. A magnetic resonance (MR) system configured to generate an external magnetic field, the MR system comprising:
   a couch; and
   a direct current (DC) motor configured to adjust and/or displace the couch, wherein the DC motor includes:

a rotor which is rotatable about a rotation axis and has first and second windings;

at least four continuous rotary transmitters, wherein:

first and second rotary transmitters of the at least four continuous rotary transmitters are associated with the first winding and are configured to supply the first winding with direct current, the first rotary transmitter forming a positive pole of the first winding and the second rotary transmitter forming a negative pole of the first winding, and third and fourth rotary transmitters of the at least four continuous rotary transmitters are associated with the second winding and are configured to supply the second winding with direct current, the third rotary transmitter forming a positive pole of the second winding and the fourth rotary transmitter forming a negative pole of the second winding;

an angle sensor configured to determine an angular position of the rotor, and a controller configured to control the DC feed to at least one of the first and second windings based on the angular position of the rotor, wherein the motor is oriented relative to the external magnetic field during operation such that the rotation axis extends transversely to the external magnetic field.

17. A method for operating a direct current (DC) motor in an external magnetic field, comprising:

placing the motor in an externally-generated magnetic field of a magnetic resonance scanner, such that a rotation axis of the motor extends transversely to field lines of the externally-generated magnetic field, wherein the motor includes: a rotor which is rotatable about the rotation axis and has first and second windings, at least four continuous rotary transmitters, wherein:

first and second rotary transmitters of the at least four continuous rotary transmitters are associated with the first winding and are configured to supply the first winding with direct current, and an angle sensor configured to determine an angular position of the rotor, the first rotary transmitter forming a positive pole of the first winding and the second rotary transmitter forming a negative pole of the first winding, and third and fourth rotary transmitters of the at least four continuous rotary transmitters are associated with the second winding and are configured to supply the second winding with direct current, the third rotary transmitter forming a positive pole of the second winding and the fourth rotary transmitter forming a negative pole of the second winding;

applying current to at least one of the first and second windings to generate a Lorentz force to cause the rotor to rotate about the rotation axis;

determining, by the angle sensor, a current angular position of the rotor;

adapting, by a controller of the motor, an application of current to the first and second windings, based on the determined current angular position, such that the rotor assumes a predetermined angular position.

18. The method as claimed in claim 17, wherein the adaptation of the application of the current comprises a short-circuiting of at least one of the first and second windings or adapting the current strength in the first and second windings.

* * * * *